United States Patent
Mitarai et al.

(10) Patent No.: US 9,102,957 B2
(45) Date of Patent: Aug. 11, 2015

(54) METHOD FOR DEGRADING ORGANIC MATERIAL USING MOTHER CELL LYASES FORMED IN ASSOCIATION WITH SPORE FORMATION OF MICROORGANISM

(75) Inventors: Kaoru Mitarai, Oita (JP); Yoji Nagahama, Tokyo (JP)

(73) Assignee: Meisho Co., Ltd., Saiki-Shi, Oita (JP)

( * ) Notice: Subject to any disclaimer, the term of this patent is extended or adjusted under 35 U.S.C. 154(b) by 0 days.

(21) Appl. No.: 13/576,921

(22) PCT Filed: Feb. 7, 2011

(86) PCT No.: PCT/JP2011/052553
§ 371 (c)(1),
(2), (4) Date: Aug. 2, 2012

(87) PCT Pub. No.: WO2011/096567
PCT Pub. Date: Aug. 11, 2011

(65) Prior Publication Data
US 2012/0301929 A1    Nov. 29, 2012

Related U.S. Application Data

(60) Provisional application No. 61/301,737, filed on Feb. 5, 2010.

(51) Int. Cl.
| | | |
|---|---|---|
| *C12P 7/10* | (2006.01) | |
| *C12P 1/04* | (2006.01) | |
| *A01N 63/02* | (2006.01) | |
| *A61K 8/66* | (2006.01) | |
| *A61Q 7/00* | (2006.01) | |
| *A61Q 19/00* | (2006.01) | |
| *A61Q 19/02* | (2006.01) | |
| *A61Q 19/08* | (2006.01) | |
| *A61K 8/99* | (2006.01) | |
| *B09B 3/00* | (2006.01) | |
| *B09B 5/00* | (2006.01) | |

(52) U.S. Cl.
CPC . *C12P 7/10* (2013.01); *A01N 63/02* (2013.01); *A61K 8/66* (2013.01); *A61K 8/99* (2013.01); *A61Q 7/00* (2013.01); *A61Q 19/004* (2013.01); *A61Q 19/02* (2013.01); *A61Q 19/08* (2013.01); *B09B 3/00* (2013.01); *B09B 5/00* (2013.01); *C12P 1/04* (2013.01); *Y02E 50/16* (2013.01)

(58) Field of Classification Search
None
See application file for complete search history.

(56) References Cited

FOREIGN PATENT DOCUMENTS

| | | | | |
|---|---|---|---|---|
| CN | 1729286 A | | 2/2006 | |
| CN | 100393672 | * | 6/2008 | ............. C05F 17/00 |
| CN | 101240313 | * | 8/2008 | ............. C12P 21/06 |
| CN | 101564081 A | | 10/2009 | |
| JP | H08-224593 A | | 9/1996 | |
| JP | H10-137727 A | | 5/1998 | |
| JP | H10-245290 A | | 9/1998 | |
| JP | 2000-102378 A | | 4/2000 | |
| JP | 2000-342248 B2 | | 12/2000 | |
| JP | 2003-095775 A | | 4/2003 | |
| JP | 2003-284586 A | | 10/2003 | |
| WO | 2010-095463 A1 | | 8/2010 | |

OTHER PUBLICATIONS

Japanese Patent Office—International Searching Authority, International Search Report mailed May 10, 2011, PCT/JP2011/052553, 8 pages.

* cited by examiner

*Primary Examiner* — Suzanne M Noakes
(74) *Attorney, Agent, or Firm* — Haynes and Boone, LLP

(57) ABSTRACT

Provided is a method for degrading an organic material. Also provided is a useful low-molecular organic material. The method for degrading an organic material is characterized by comprising a step for preparing the organic material to be degraded, and a step for treating said organic material with mother cell lytic enzymes which are formed through cytolysis associated with the spore formation of a spore-forming aerobic bacterium.

18 Claims, 6 Drawing Sheets

METHOD FOR DEGRADING ORGANIC MATERIAL USING MOTHER CELL LYASES FORMED IN ASSOCIATION WITH SPORE FORMATION OF MICROORGANISM

CROSS-REFERENCE TO RELATED APPLICATIONS

This application claims priority under 35 U.S.C. §119 and 35 U.S.C. §365 to U.S. Provisional Application No. 61/301,737, filed Feb. 5, 2010, and PCT Intl. Pat. Appl. No. PCT/JP2011/052553, filed Feb. 7, 2011; the contents of each of which is specifically incorporated herein in its entirety by express reference thereto.

FIELD OF THE INVENTION

The present invention relates to a method for degrading an organic material using a mother cell degrading enzyme group secreted from a microorganism or a group of microorganism, especially a method for degrading the organic material using spore-forming aerobic bacteria consisting of multiple endospore-forming aerobic bacteria.

BACKGROUND OF THE INVENTION

Degradation of an organic material by a microorganism has been widely used by human beings before and after the beginning of recorded history by means of fermentation of food using a lactic acid bacterium, a yeast, *Aspergillus*, or *Bacillus*. Particularly in recent years, as described in patent reference 1, we have used *Bacillus* to degrade sanitary sewage, garbage, etc. and have formed compost (farmyard manure) for agriculture. Also as described in patent reference 2, a method for degrading an organic material including for example, a shell of a crab or a shrimp, or cellulose by a thermophile has been developed. In addition, applied research progresses at a rapid pace, wherein a microorganism having a new function is created by introducing genes with multiple functions to the thermophile, the yeast, and *Bacillus*.

In the meantime, these traditional degrading methods using an organic material only uses a digestive enzyme with "limited functions" secreted from bacterial base (nursing cell) because the bacterium digests and absorbs necessary nutrition. In other words, these degrading methods utilize a degradative enzyme for digestion necessary for daily living of a bacterium, but do not utilize an enzyme group used for cytolysis homological to autophagy, which is used for survival under starvation state or insufficient oxygen of culture environment, or powerful and versatile bulk degradative enzyme groups released in apoptosis induction to protect an individual in a multicellular creature. Also, these degrading methods have a drawback that, due to the utilization of bacterial body, the changes of living or culture conditions of a bacterium alters the secreted enzymes which, in turn, diminish safety of degradation, and there is a need for versatile innovation to maintain these living or culture conditions of a bacterium.

On the other hand, other methods, in which a degradative enzyme (digestive enzyme) is isolated from a bacterium and used, including disposer using an enzyme, have been developed, and like the above method, these are trying to utilize individual function of the digestive enzyme secreted from a nursing cell against a specific organic material. For example, in patent reference 3, a method for degrading collagen with an enzyme is disclosed and the method also simply utilizes a digestive enzyme. Currently, these approaches shift to methods in which a new enzyme is provided through introduction of a functional gene and are especially applied to medical field, and research on gene transfection of a degradative enzyme with single function secreted from a nursing cell of a thermophile is caught on. However, these approaches also only utilize a traditional digestive degradative enzyme.

The technology related to a bacterial group or a symbiotic bacterial group includes that of patent reference 4, but it also only utilizes a nutrition-digestive degradative enzyme group secreted from a nursing cell.

PRIOR ART DOCUMENTS

Patent Reference

Patent reference 1: Japanese Laid-Open Patent Publication No. H08 (1996)-224593
Patent reference 2: Japanese Patent No. 3146305
Patent reference 3: Japanese Laid-Open Patent Publication No. 2003 -284586
Patent reference 4: Japanese Laid-Open Patent Publication No. H10 (1998)-245290

SUMMARY OF THE INVENTION

The present invention was performed considering the above situation, and the purpose of the invention is to provide a method for degrading an organic material using a bulk degradative enzyme group (mother cell lytic enzymes) related to cell lysis of a mother cell, which has not been used to date and is associated with the spore formation of an endospore (spore)-forming aerobic bacterium (prokaryotic microorganism). In addition, the purpose of the present invention is to provide a useful low-molecular organic material using this degrading method.

The inventors compered nutrient medium of an MRE symbiotic aerobic bacterium group and solution after the spore formation; as a result, discovered that remarkable difference exists between both degrading power of an organic material; and completed this invention as a result of further devoted research and experiment.

Until recently, an organic material is degraded and applied through fermentation using a digestive degradative enzyme (including oxidoreductase, convertase, etc.) secreted daily by a cultured cell (mother cell) of a prokaryotic microorganism including aerobic *Bacillus* and thermophilic *Bacillus*. However, this fermentation of the cultured cell is ultimately aimed at ingesting nutrition of a bacterium; therefore, every useful low-molecular organic materials formed from decomposition are digested and absorbed by the cultured cell (mother cell); and little or nothing useful residues are left.

On the other hand, nobody had thought that formation of an endospore (spore) may be initiated by cutting out nutrition of a culture medium of an endospore-forming aerobic bacterium and cutting off air, and clear remained liquid after precipitation of the formed endospore (spore) may have some effect. The reason for that is because the cultured cell (mother cell) which is a base of fermentation cannot exist and dies off, and it is difficult to assume that the endospore (spore) enveloped by hard shell containing dipicolinic acid may degrade an organic material.

However, the inventors discovered that by filtering a solution after precipitation of the formed endospore through a 0.2-μm membrane and a 0.02-μm filter, eliminating infinitesimal remained cultured cells and residual floating endospores (spores), and aerating the solution, the solution has powerful degrading power. Furthermore, the degrading power is found to be more powerful than that of the cultured cell.

Therefore, according to the first principal aspect of this invention, a method for degrading an organic material comprising a step for preparing the organic material to be degraded, and a step for applying mother cell lytic enzymes which are formed through cytolysis associated with the spore formation of a spore-forming aerobic bacterium to the organic material is provided.

Such framework may provide a method for degrading an organic material effectively. The present invention may also provide a method for easily degrading an organic material with high lignin content which was difficult to decompose. Furthermore, the present invention may degrade a refractory organic material or an organic material harmful to human and environment.

Also, according to such framework, a degraded product may be used as a chemical herbicide or a beauty essence.

According to an embodiment of the invention, in these methods, the spore-forming aerobic bacterium is a group of mixed bacteria consisting of multiple endospore-forming aerobic bacteria. In this case, the group of mixed bacteria is preferably an MRE symbiotic bacterium group.

According to another embodiment of the invention, these methods further comprising applying spores formed through the spore formation of the spore-forming aerobic bacterium to the organic material, wherein the spores produce mother cell lytic enzymes through germination and re-sporulation, are provided.

In this case, it is preferable that the organic material to be degraded is immersed in a decomposing solution containing the mother cell lytic enzymes and/or the spores, and the solution is decomposed through aeration. And the organic material to be degraded is selected from a group consisting of *Ganoderma lucidum, Agaricus Blazei* Murill, *Cordyceps Sinensis* Berkeley Saccardo, Chaga, and fish scale, and these decomposed products are used as a natural immunity activating composition. Especially, when the organic material to be degraded is fish scale, a decomposed product of this fish scale may be used as a natural immunity activating beauty essence.

In addition, according to another embodiment of the invention, in the method using the spore, the organic material to be degraded is stirred in the presence of air under the condition of 60-80° C., and the mother cell lytic enzymes and/or the spore-containing degradation solution is decomposed through dissemination In this case, it is preferable that this method further comprises a step for applying an organic materials with high lignin content selected from a group consisting of rice hull and sawdust as fluid bed. The above temperature is preferably 64-68° C.

According to another embodiment of the invention, the method is performed using an apparatus comprising: a decomposition tank comprising a horizontal axis of rotation, to which one or more arms with a fixed stirring plate are installed, adapted to form a heating plate along a trajectory of the stirring plate; a heater which is able to regulate temperature of the heating plate between 60-160° C.; and a nozzle installed at the top of the decomposition tank, spraying a decomposition solution containing the mother cell lytic enzymes and/or the spores.

Furthermore, according to another embodiment of the invention, in these methods, the organic material to be degraded is soybean curd refuse, and a decomposition product of the soybean curd refuse is used as a chemical herbicide.

According to another embodiment of the invention, in these methods, the organic material to be degraded is a material including at least lignin and cellulose, such as bamboo, wood, lumber obtained from thinning, rice straw, and a decomposition product of the material is used as a raw material of ethanol.

Characteristics and distinguished effect/efficacy of the invention other than those above will be apparent to those of skill in the art by referring the following embodiment and drawings of the invention.

DETAILED DESCRIPTION OF THE INVENTION

Figure 1:
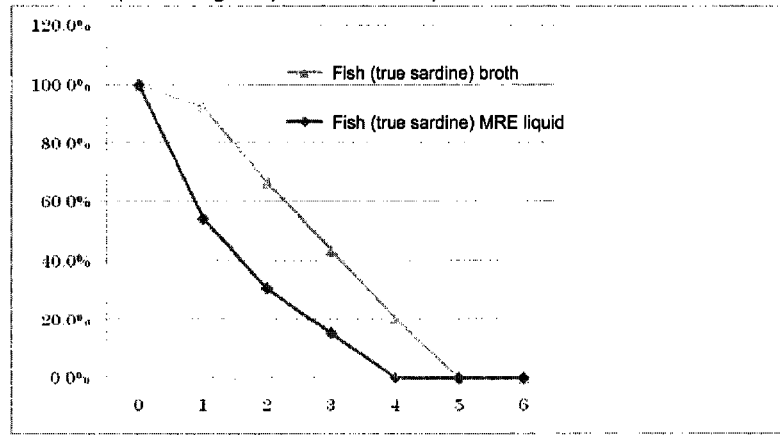
FIG. 1 is a graph showing comparison of decomposition when "true sardine" is degraded in one embodiment of the invention.

As described above, the present invention provide a method for degrading an organic material using mother cell lytic enzymes released on cell lysis of a mother cell associated with sporulation of a endospore (spore)-forming aerobic bacterium. The aerobic bacterium is not limited, if it forms an endospore, and preferably, is MRE symbiotic bacterial group. The aerobic bacterium used in a method related to the present invention may be a mixed bacterium group consisting of one or more aerobic bacterium.

The MRE symbiotic bacterial group comprises *Bacillus* sp. (FERM BP-11209, identification no. MK-005), *Lysinibacillus fusiformis* (FERM BP-11206, identification no. MK-001), *Bacillus sonorensis* (identification no. MK-004), *Lysinibacillus* sp. (FERM BP-11207, identification no. MK-002), and *Comamonas* sp. (FERM BP-11208, identification no. MK-003), all of which are aerobic bacteria.

The method related to the invention uses the step in which an organic material is degraded effectively by filtering a solution after precipitation of the formed endospore through a 0.2-μm membrane and a 0.02-μm filter, removing infinitesimal residual cultured cells and residual floating endospores (spores), and aerating the solution. The inventors discovered that the solution has powerful degrading power and completed the invention.

As a more detailed explanation, 1 m$^3$ of cultured medium of an MRE symbiotic bacterium group (MK-001, MK-002, MK-003, MK-004, MK-005), which is a group of aerobic bacteria forming the above endospores, is added to two same-shaped 1.2-m³ culture containers, and aerated to make dissolved oxygen level 0.5 mg/L-1.2 mg/L. One is named as a culture cell tank and the other is named as a sporulation tank. To the culture cell tank, 500 g of fish flour, 500 g of rice bran, 250 g of oil meal, and 50 g of meat juice were added as minimal nutrition to continue culture with aeration under the culture condition of culture pH 6.0-6.8 and culture temperature 25-35° C. In contrast, the sporulation tank is placed under starvation state without any nutrition, and continues to receive aeration under the condition of 25-30° C. to initiate endospore formation utilizing depletion of nitrogen component as a trigger. After clarity of the culture medium is increased, aeration (oxygen supply) is stopped, and then the endospore concurrently initiates precipitation to make clear solution. The solution was filtered with 0.2-μm membrane and next with 0.02-μm filter, added to the sporulation tank washed well again to get degrading-power experiment organized. Here, we call a solution of sporulation of MRE bacteria, of which residual mother cells and spores are eliminated by filtration, MRE filtrate. Therefore, the MRE filtrate has very few bacteria and spores, but the MRE filtrate has mother cell lytic enzymes. The invention utilizes the power of the mother cell lytic enzymes degrading an organic material. In this specification, "MRE filtrate," "post-sporulation solution," "post-sporulation solution without bacteria" are used and all refer to a solution comprising mother cell lytic enzymes unless otherwise specified.

In the present invention, the sizes of membrane and filter applied to the above solution are not just limited. For example, the membrane may be 1 μm, 0.7 μm, 0.5 μm, 0.3 μm, and preferably, 0.2 μm. In addition, the filter may be 0.15 μm, 0.1 μm, 0.07 μm, 0.05 μm, 0.03 μm, and preferably 0.02 μm.

In the present invention, using the two culture cell tank and sporulation tank described above, aeration was performed until both concentration of residual oxygen reached to 0.5 mg/L-1.2 mg/L, and the following experiment was performed.

For three materials, "true sardine," "pork," and "*Agaricus Blazei* Murill," two pairs of each materials having similar weight, section, and shape as much as possible were prepared, immersed into the culture cell tank and the sporulation tank filled with liquid with finely-woven nets of same weight, and took off at regular time intervals to weigh under same condition after removal of moisture using thick paper kitchen towel, to examine and compare each degrading power.

The result of the decomposition of "true sardine" is as following:

TABLE 1

| | True Sardine | | |
|---|---|---|---|
| Day | Culture medium | MRE filtrate | Difference of decomposition |
| 0 | 100% | 100% | 0.00 |
| 1 | 92.3% | 54.2% | 0.38 |
| 2 | 66.7% | 30.5% | 0.36 |
| 3 | 43.6% | 15.3% | 0.28 |
| 4 | 20.5% | 0% | 0.21 |
| 5 | 0% | 0% | 0 |
| 6 | 0% | 0% | 0 |

Figure 2:
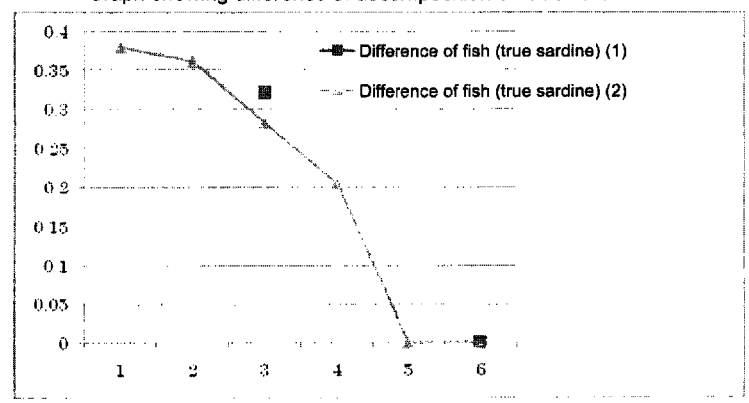
FIG. 2 is a graph showing difference of decomposition when "true sardine" is degraded in one embodiment of the invention.

FIG. 1 shows a graph of comparison of decomposition and FIG. 2 shows a graph of decomposition difference. In the comparison of decomposition of "true sardine," it defied common sense and it was not only shown that the MRE filtrate was decomposable but also shown that the MRE filtrate having almost no residual bacterium or spore had more degrading power than culture medium which develops bacteria. The result was surprising, wherein 20.5% of true sardine was left undecomposed in usual culture medium tank at Day 4, while whole "true sardine" including bones was decomposed in clear MRE filtrate with almost no bacteria and spores.

The result of decomposition of "pork" is as following:

TABLE 2

| | Pork | | |
|---|---|---|---|
| Day | Culture medium | MRE filtrate | Difference of decomposition |
| 0 | 100% | 100% | 0 |
| 1 | 74.0% | 43.2% | 0.31 |
| 2 | 48.8% | 21.4% | 0.27 |
| 3 | 34.4% | 11.1% | 0.23 |
| 4 | 22.3% | 5.4% | 0.17 |
| 5 | 19.8% | 0% | 0 |
| 6 | 14.0% | 0% | 0 |

Figure 3:
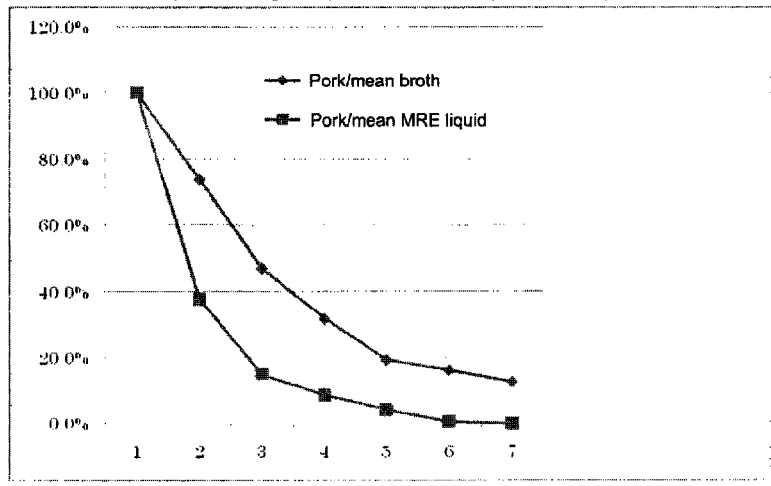
FIG. 3 is a graph showing comparison of decomposition when "pork" is degraded in one embodiment of the invention.
Figure 4:
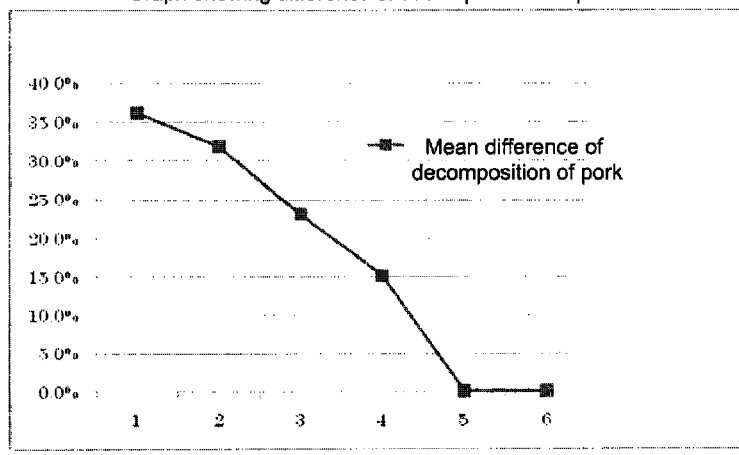
FIG. 4 is a graph showing difference of decomposition when "pork" is degraded in one embodiment of the invention.

FIG. 3 shows a graph showing comparison of decomposition and FIG. 4 shows a graph of decomposition difference. In "pork," same result as "true sardine" was obtained. After 5 days, decomposed product remained in the culture medium tank was 19.8%, while the product was completely decomposed in the MRE filtrate.

The following table shows the more detailed result measuring degrading power of culture medium and MRE filtrate for "pork."

TABLE 3

| | Pork | | | | | | | | | | | |
|---|---|---|---|---|---|---|---|---|---|---|---|---|
| | 1 | | 2 | | 3 | | 4 | | 5 | | Pork/mean | |
| Day | Culture medium | MRE filtrate | Culture medium | MRE filtrate | Culture medium | MRE filtrate | Culture medium | MRE filtrate | Culture medium | MRE filtrate | Culture medium | MRE filtrate |
| 0 | 43.0 | 44.8 | 60.0 | 57.8 | 61.0 | 60.0 | 57.0 | 58.2 | 51.0 | 51.3 | 54.4 | 54.4 |
| 1 | 32.4 | 15.0 | 48.2 | 20.5 | 43.2 | 23.5 | 38.4 | 20.5 | 38.4 | 23.0 | 40.2 | 20.5 |
| 2 | 21.0 | 6.1 | 32.8 | 8.8 | 25.7 | 8.6 | 24.1 | 8.1 | 24.2 | 9.5 | 25.6 | 8.2 |
| 3 | 14.6 | 3.2 | 21.9 | 6.8 | 16.6 | 2.4 | 14.5 | 5.2 | 18.4 | 5.7 | 17.2 | 4.7 |
| 4 | 9.3 | 1.9 | 12.8 | 5.1 | 11.5 | 1.3 | 8.8 | 0.8 | 10.0 | 2.2 | 10.5 | 2.3 |
| 5 | 8.5 | 0.0 | 10.0 | 1.7 | 10.0 | 0.0 | 6.4 | 0.0 | 9.0 | 0.0 | 8.8 | 0.3 |
| 6 | 6.0 | 0.0 | 8.0 | 0.0 | 8.0 | 0.0 | 5.2 | 0.0 | 7.0 | 0.0 | 6.8 | 0.0 |

The following table makes it possible to compare the result in percentage.

TABLE 4

| | Pork | | | | | | | | | | | |
|---|---|---|---|---|---|---|---|---|---|---|---|---|
| | 1 | | 2 | | 3 | | 4 | | 5 | | Pork/mean | |
| Day | Culture medium | MRE filtrate | Culture medium | MRE filtrate | Culture medium | MRE filtrate | Culture medium | MRE filtrate | Culture medium | MRE filtrate | Culture medium | MRE filtrate |
| 0 | 100.0% | 100.0% | 100.0% | 100.0% | 100.0% | 100.0% | 100.% | 100.0% | 100.0% | 100.0% | 100.0% | 100.0% |
| 1 | 76.0% | 33.5% | 80.3% | 35.5% | 70.8% | 39.2% | 67.4% | 35.2% | 75.3% | 44.8% | 73.9% | 37.7% |
| 2 | 48.8% | 13.6% | 54.7% | 15.2% | 42.1% | 14.3% | 42.3% | 13.9% | 47.5% | 18.5% | 47.0% | 15.1% |
| 3 | 34.0% | 7.1% | 36.5% | 11.8% | 27.2% | 4.0% | 25.4% | 8.9% | 36.1% | 11.1% | 31.6% | 8.6% |
| 4 | 21.6% | 4.2% | 21.3% | 8.8% | 18.9% | 2.2% | 15.4% | 1.4% | 19.6% | 4.3% | 19.3% | 4.2% |
| 5 | 19.8% | 0.0% | 16.7% | 2.9% | 16.4% | 0.0% | 11.2% | 0.0% | 17.6% | 0.0% | 16.1% | 0.6% |
| 6 | 14.0% | 0.0% | 13.3% | 0.0% | 13.1% | 0.0% | 9.1% | 0.0% | 13.7% | 0.0% | 12.6% | 0.0% |

The difference of degrading power is as following:

TABLE 5

| | Pork | | | | | |
|---|---|---|---|---|---|---|
| Day | 1 Difference | 2 Difference | 3 Difference | 4 Difference | 5 Difference | Mean Difference |
| 1 | 42.6% | 44.9% | 31.7% | 32.1% | 30.5% | 36.2% |
| 2 | 35.2% | 39.4% | 27.8% | 28.4% | 28.9% | 31.9% |
| 3 | 26.8% | 24.7% | 23.2% | 16.5% | 25.0% | 23.1% |
| 4 | 17.4% | 12.5% | 16.7% | 14.1% | 15.3% | 15.1% |
| 5 | 0.0% | 13.7% | 0.0% | 0.0% | 0.0% | 3.0% |
| 6 | 0.0% | 0.0% | 0.0% | 0.0% | 0.0% | 0.0% |

It is found that the degrading power is obviously different between the culture medium and the post-sporulation solution without bacteria.

The result of decomposition of "*Agaricus Blazei* Murill" is as following:

TABLE 6

| | *Agaricus Blazei* Murill | | |
|---|---|---|---|
| Day | Culture medium | MRE filtrate | Difference of decomposition |
| 0 | 100% | 100% | 0.00 |
| 2 | 94.5% | 72.0% | 0.22 |
| 5 | 72.1% | 58.5% | 0.14 |
| 10 | 48.0% | 34.6% | 0.13 |
| 16 | 9.5% | 0% | 0.09 |

Figure 5:
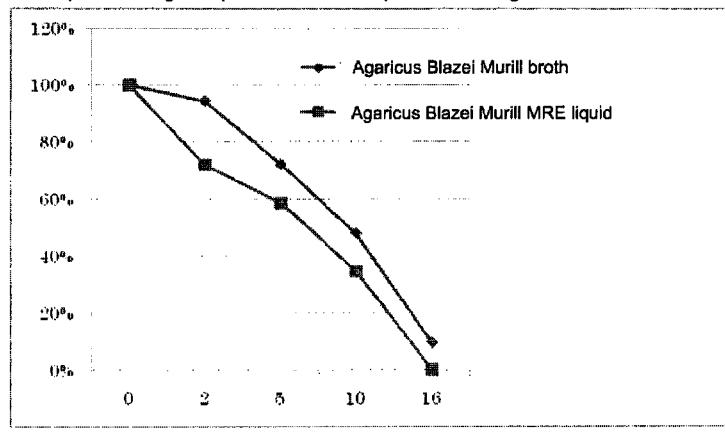
FIG. 5 is a graph showing comparison of decomposition when "*Agaricus* Blazei Murill" is degraded in one embodiment of the invention.
Figure 6:
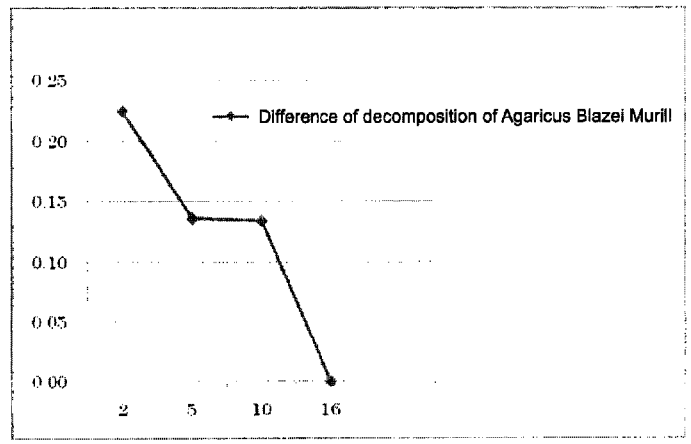
FIG. 6 is a graph showing difference of decomposition when "*Agaricus* Blazei Murill" is degraded in one embodiment of the invention.
Figure 7:
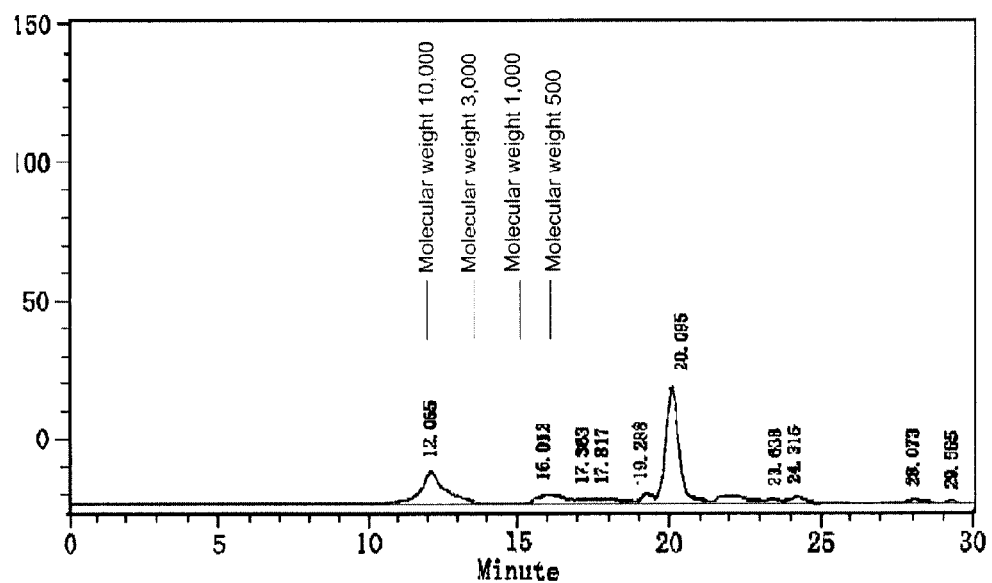
FIG. 7 is a graph showing distribution of molecular weight of degraded products from decomposition of "*Agaricus Blazei* Murill" in one embodiment of the invention.

FIG. 5 shows a graph of comparison of decomposition and FIG. 6 shows the graph of decomposition difference. FIG. 7 shows a graph of molecular weight distribution of degraded products of *Agaricus Blazei* Murill analyzed by HPLC

*Agaricus Blazei* Murill is a bacterium having glycan layer or chitin layer which is resistant to decomposition by microorganism. Therefore, the bacterium has a characteristic that bacterial body is destroyed only after a certain level of low-molecular material forms, even if decomposition process goes off. Thus, the decomposition speed of *Agaricus Blazei* Murill is slow in either the culture medium tank or sporulation tank. In Agaricus, it was not only confirmed that decomposition actually occur in MRE filtrate with almost no bacteria and spores, but also shown that degrading power of MRE filtrate is stronger.

The result of decomposition of "scale of sea bream" is as following:

TABLE 7

| | Scale of sea bream | | |
|---|---|---|---|
| Day | Culture medium | MRE filtrate | Difference of decomposition |
| 0 | 100% | 100% | 0.00 |
| 2 | 98.4% | 85.2% | 0.14 |
| 5 | 95.9% | 85.0% | 0.11 |
| 10 | 91.7% | 82.1% | 0.10 |
| 16 | 89.1% | 78.0% | 0.11 |
| 22 | 86.4% | 68.5% | 0.18 |

Figure 8:
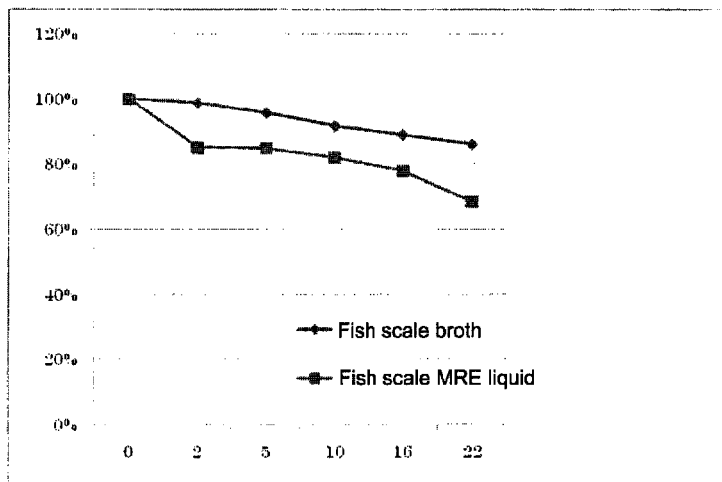
FIG. 8 is a graph showing comparison of decomposition when "scale of sea bream" is degraded in one embodiment of the invention.
Figure 9:
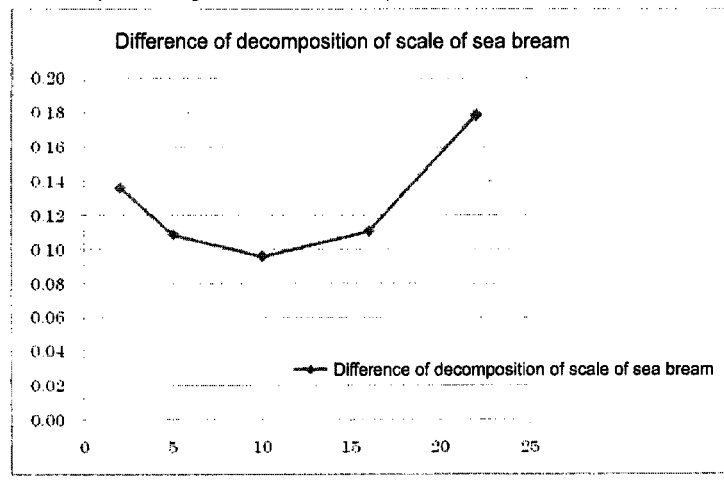
FIG. 9 is a graph showing difference of decomposition when "scale of sea bream" is degraded in one embodiment of the invention.
Figure 10:
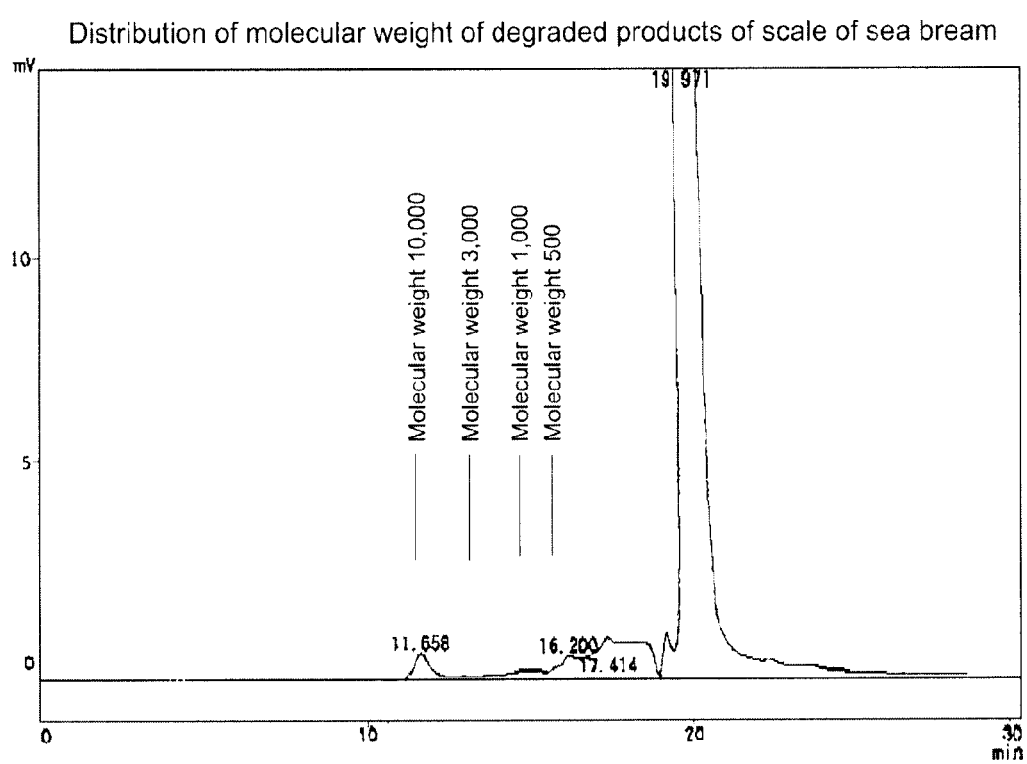
FIG. 10 is a graph showing distribution of molecular weight of degraded products from decomposition of "scale of sea bream" in one embodiment of the invention.

FIG. 8 shows a graph of comparison of decomposition comparison FIG. 9 shows a graph of decomposition difference. FIG. 10 shows a graph of molecular weight distribution of decomposed scale of sea bream analyzed by HPLC.

The "scale of sea bream" having more robust tissue, which collagen tissue binds to apatite, has slow decomposition speed for both. However, the MRE filtrate was shown to have more powerful degrading power than the culture medium. The difference of decomposition at day 10 was at the lowest and then increased to be the highest at day 22; and for this reason, it was thought that minimal spore sneak through a filter, germinated using degrading product of sea bream collagen as nutrition, and increased degrading power by re-supplying mother cell lytic enzymes through re-sporulation to amplify the difference of the degrading power.

From these series of experiment, the inventors discovered that the endospore-forming aerobic bacterium have powerful degrading ability of an organic material in solution left after sporulation. For the first time, the fact that aeration increases the degrading power was also found. Therefore, in the present invention, the spore formed by sporulation of a spore-forming aerobic bacterium produces mother cell lytic enzymes through germination and re-sporulation. The "germination" in the specification refers to the initiation of activity from resting state of spores of fungi or inactive state such as state of apparent death.

The degrading method using post-sporulation solution has an even greater advantage. It is a nature that low-molecular substances such as oligopeptide or oligosaccharide chain formed during decomposition remain as useful material not absorbed by a bacterium such as in culture medium. We can create various useful materials using this nature.

Here, special enzyme group which fuses a base formed during sporulation process is mentioned. The reason is because the secret of the difference of degrading power between culture medium and MRE filtrate is hidden.

In an example of anaerobic gram-positive bacterium, the process of endospore formation is started to work by deficiency of nitrogen as a trigger, and the sporulation process proceeds. After 2-3 hours has elapsed, it cannot go back to a nursing cell even if nitrogen or nutrition is given. It means that the state of a nursing cell which goes about its daily life at gene expression level has shifted to the state of crisis management, sporulation. This happened because the spores are enwrapped by many layers of strong hard shell and can resist under severe situation including drying, high temperature (120-160° C.), high pressure, vacuum, variation of pH, radiation. If growth cycle of a nursing cell slows down due to deficiency of nitrogen and exceed a certain limit (for example, one division per two hours in $B.\ megaterium$), a nursing cell cannot be retained and sporulation is actively done.

In the first step of the sporulation, gene cluster (Spo0, Spo0a, Spo0b, Spo0c, etc.) functions and nucleus aggregates to become axon-like shape. In the second step, a gene cluster (SpoI) functions and membrane separating a spore and a mother cell forms and becomes a prespore. In the third and fourth steps, gene cluster (SpoII, SpoIII) functions, cortex comprising peptide glycan and the like as a major component (same structure as cell wall) wraps spore-forming portion, and a forespore forms. In this step, it cannot return to a nursing cell which means irreversible. Of note, through these four steps, a peptidic antibacterial agent with about 1,400 dalton of molecular weight is secreted. In the next fifth and sixth steps, gene cluster (SpoIV, SpoV) functions, uptake of large amount of Ca ion and synthesis of large amount of dipicolinic acid which chelates Ca proceed, and very strong spore coat in the state of high level of dehydration is formed over the cortex. The spore coat is damage-tolerant to heat and radiation/ultraviolet light, and works to protect a spore effectively from an enzyme or a chemical. The spore also can survive under high pressure or vacuum. The spore coat is characterized by having special optical property, double refraction, and being distinguished by phase microscope. In the last seventh steps, release of spores (endospores) and mother cell cytolysis occur and the sporulation reaches its completion.

Bulk degradative enzyme groups produced on this mother cell cytolysis seem to generate the difference of degrading power between culture medium of nursing cells and MRE filtrate after sporulation. This is because an enzyme group for digestion and absorption of nutrition secreted from a nursing cell of culture medium in daily life is essentially different from the mother cell lytic enzymes secreted facing with crises of a life. The difference is obvious on the assumption that a cell never secretes an enzyme which causes autocytolysis in daily life. The mother cell lytic enzymes are homologous to lysosome group of an animal or processing enzyme group of a plant as well as an enzyme group including papain produced when fruit grows into ripe one or a special enzyme appearing in sperm development of an animal, which are the result of molecular evolution of the mother cell lytic enzymes. The processing enzyme group of a plant is a group of enzyme that works in vacuole of a plant cell.

Here, the lysosome enzyme group which work in autophagy (bulk type decomposition in an old intracellular organ) and the degrading enzyme group which functions in the process of apoptosis (programmed natural death) are thought to go through molecular evolution having mother cell lytic enzymes released in the process of sporulation (endosporulation) used in this invention as an ancestor, with processing enzyme group which works in vacuole of a plant. These mother cell lytic enzymes are known to be the degrading enzyme which emerges facing with crises of a life or when biological defense/intracellular detoxication proceeds, not in daily vital activity. This has medically important meanings.

For the lysosome enzyme group, the category is said to exceed 50, and it is known that lack of certain degrading enzyme (lysosome-type degrading enzyme) gene develops serious genetic disorder and autophagy or apoptosis do no work in an old cell. In the same manner, the lysosome enzyme is known to cause various diseases when it leaks out from a cell. Therefore, human lysosome enzyme or its inhibitor is used as a diagnostic marker of various diseases, and in certain diseases, these degrading enzymes have been gradually used with a specific substance as its target. For example, when treating mucopolysaccharidosis, human mucopolysaccharide degrading enzyme is used in treatment after its phosphorylation.

The lysosome enzyme group is known to work in autophagy in which intracellular waste organ and waste material is degraded, in apoptosis in which a degenerated cell like cancer is get suicided, and as an enzyme which degrades bacteria or virus breaking into a cell. The lysosome is also a bulk-type degrading enzyme which do not have one action like general digestive enzyme or metabolic enzyme, but degrade waste organ or a cell itself in block in collaboration to more than 50 types of enzyme groups The nature is different from that of a digestive degrading enzyme; it is said that some enzymes have a nature that increases activity in mild acidity field and at higher temperature than a digestive enzyme and 5,000-10,000 times higher degrading power than a digestive enzyme.

The enzymes known to be in lysosome enzyme group include nucleolytic enzyme including ribonuclease/deoxyribonuclease; powerful and multifunctional protease including cathepsin from collagen-degrading enzyme, cathepsin D and cathepsin E from aspartic protease, cathepsin K, cathepsinB, and cathepsin S from cysteine protease, cathepsin G from serine protease, cathepsin H from aminopeptidase; and further, arylsulfatase, β-glucuronidase, esterase, and acid phosphatase; in glycosylase, sphingolipid degrading α-galactosidase, β-hexosaminidase A and B, arylsulfatase A, galactosylceramidase, glucosylceramidase, acid sphingomyelinase, acid ceramidase, etc.; glycoprotein degrading α-fucosidase, α- and β-mannosidase, neuraminidase, aspartyldu-cosaminidase, α-N-acetyl galactosaminidase, etc.; mucoperiosteum degrading α-iduronidase, iduronate sulfatase, heparan N sulfatase, α-N-acetylglucosaminidase, 6-sulfatase, galactose 6-sulfatase, β-galactosidase, allylsulfatase B, β-glucuronidase, etc.; and cholesteryl ester and lipid degrading enzyme such as acid lipase; and further importantly, degrading enzymes including muramidase, mucopeptide hydrolase, and acylamide amidohydrolase (amidase) which degrade peptide glycan layer forming cell wall of pathogenic prokaryotic microorganism; all of which are elucidated to exist. It is also suggested that oxidoreductase group have an important role.

As described above, endospore-forming aerobic gram-positive bacterium and gram-negative mother cell lytic enzymes are homologous enzymes to lysosome enzyme which protects life and inhibits aging and vacuole processing enzyme of a plant, and molecular ancestor of these.

These enzyme groups have completely different nature from an enzyme group which aims at digestion and is secreted from a nursing cell to maintain living. These enzyme groups are bulk-type degrading enzyme which has general property and is released for the purpose of survival under situation of starvation environment, and therefore, have powerful degrading power which can degrade all organs and contents of a cell.

This survival maintenance function has consistently same principle from cytolysis of prokaryote to autophagy or apoptosis which occur under starvation environment of human.

As an example of difference of these enzyme groups, if you look into collagen degrading enzyme, protease which is usual protein-degrading enzyme cannot degrade collagen, and therefore, collagenase (MMP1) takes charge of degrading collagen for ingesting nutrition within daily living of animate beings. However, this collagenase (MMP1) can degrade fibrous form collagen type I, type II, and Type III, but cannot degrade membranal collagen type IV or fiber-adjusting collagen V. Collagen type IV is a survival maintenance collagen which permit transit of low-molecular compound and inhibit protein passing as well as inhibit entry of an enzyme which cannot be degraded by usual collagen. However, in lysosome of organism at higher level than eukaryote and bulk enzyme group of lysosome homologous vacuole, cathepsin L and similar collagen-degrading enzyme (MMP2 and MMP3) can degrade this membranal collagen type IV. In particular, cathepsin L is true bulk type enzyme (general-purpose enzyme) which can degrade type I to type V. The major feature of this invention is trying to use the bulk type enzyme group related to this survival and one of the mainstay of means for solving the problems.

Here, collagen type I is extracellular matrix-forming collagen and constitutes bone, dentinal matrix, and cement, as well as skin, tendon, fascia, and blood vessel. Collagen type II has flexibility and constitutes cartilage along with proteoglycan. Collagen type III has an important role in fetus tissue or arterial wall. On the other hand, collagen type IV has a role in forming basal membrane and protecting a cell or tissue. In addition, collagen type V is a type of collagen rich in amnion or placenta which has a role to back up matrix of cell surface and again protect a cell from usual MMP1.

In decomposition method of an organic material of this invention, a material that cannot be degraded by degrading enzyme secreted by a prior nursing cell can be degraded, because the enzyme can degrade collagen type IV or V.

In addition, the mother cell lytic enzymes released in association with spore forming cytolysis (especially those from an MRE symbiotic bacterium group) have enhanced ability to degrade bone tissue and scale woven up by type I collagen and apatite (a kind of calcium phosphate) at nano-level and astounding degrading ability that can directly degrade bone or giant scale in whole.

Bulk type cathepsin K, which is cysteine protease similar to papain, has ability to degrade bone or scale, along with cathepsin L from bulk-type collagen degrading enzymes and cathepsin B from cysteine protease which can degrade cellular matrix. Cathepsin B from cysteine protease is also a bulk-type degrading enzyme which works as dipeptidyl carboxypeptidase. Cathepsin E from aspartic protease is a medically important degrading enzyme associated with atopic dermatitis. Therefore, a cathepsin enzyme from papain superfamily is fairly similar to cathepsin K and a powerful assisting mean for decomposition of bone or scale by the enzyme group of this invention.

The present invention utilizes the bulk-type enzyme group, released on mother cell cytolysis homologous to these autophagy or lysosome, on decomposition of an organic material. These enzyme groups have not been used in traditional fermentation/decomposition process by a nursing cell, such as bacillus bacterium, and also, have been discarded as unnecessary treatment liquid after decomposition of sanitary sewage treatment or garbage treatment process of aerobic bacillus bacterium. The mother cell lytic enzymes have been completely set aside to date. The center of research on thermophile has been heat-resistant enzyme secreted from a nursing cell and the enzyme for a mother cell cytolysis homologous to autophagy or lysosome has been set aside.

The primary characteristic of this invention is to activate a series of sporulation gene cluster in endospore-forming aerobic bacterium when this bacterial group goes into starvation state by depletion of nutrition such as nitrogen resource including amino acid, to produce mother cell cytolysis homologous to autophagy at the last stage, and to use the mother cell lytic enzymes released at this time for powerful bulk-type decomposition into decomposition of an organic material.

The second characteristic of this invention is to get coexisted different and versatile degrading enzyme group including aerobic gram-positive and gram-negative bacterium in endospore-forming aerobic bacterium or thermophilic bacillus, and to use obtained versatile stable enzyme group having enzyme consistency for decomposition of an organic material.

The third characteristic is to use aeration in the solution after spore formation. This procedure is based on the discovery that aeration dramatically increases the decomposition power of mother cell lytic enzymes, and the rationale is thought that oxidation-reduction enzyme in the mother cell lytic enzymes works effectively along with effective agitation effect.

Moreover, the following method is to develop and enhance the effect of the method of this invention:

(A) a method for degrading an organic material using an enzyme group which adds an enzyme homologous to lysosome including papain (an enzyme homologous to cathepsin K) to mother cell lytic enzymes; and (B) a method for using the mixture of mother cell lytic enzymes and formed spores (double spore method).

The former method (A) is only to simply use an enzyme additively, but the later method (B) is an excellent method for degrading a persistent organic material in usual fermentation. This is because, as described later, the spores repeat germination and re-sporulation under the condition of high temperature, high oxygen concentration, and low nutrition, and therefore mother cell lytic enzymes are newly released through the re-sporulation more than once for resupply. In this case, it was able to find that the spores and the mother cells eventually disappear under a certain condition.

Here, including the effective double spore method, compound liquid having degrading power of an organic material which is added spores to mother cell lytic enzymes including MRE filtrate is called as "MRE degrading liquid."

Therefore, specific method for degrading an organic material of this invention include the following three methods:

(1) a method to continue aeration without nutrition supply from mixed culture medium for an aerobic spore-forming gram-positive bacterium and an aerobic spore-forming gram-negative bacterium as endospore-forming aerobic bacterium or thermophilic bacillus, and to filter the supernatant solution for decomposition after transparency improvement by spore precipitation (2) a direct method to continue aeration without nutrition supply from mixed culture medium for an aerobic gram-positive bacterium and gram-negative bacterium as an endospore-forming aerobic bacterium or thermophilic bacillus, and to degrade a material to be degraded instead of nutrition (3) a method to re-inject spores precipitated in the method (1) or (2) to the mother cell lytic enzymes obtained in the above method (1) or (2) to use the mixture of the mother cell lytic enzymes and the spores (double spore decomposition method).

In the present method, all the methods are beneficial, but the method (1) has an advantage that decomposition product having very few residue can be obtained, because purely effective enzyme group is used without intervention of bacterium and no spores are left again, and maintenance, storage, transportation, and usage are easier and highly safer. The method (2) is practically limited to a case where digestive enzyme group secreted from a nursing cell is more advantageous to decomposition and is not favorable because, in fact, degrading effect is attenuated and decomposed material is decreased.

The method (3) bring into action by using the mother cell lytic enzymes at high temperature area of 60-70° C. Particularly, it is suitable for degrading while heating and stirring an organic material to be degraded that the compound liquid of mother cell lytic enzymes and spores are sprayed at temperature under 80° C. in the environment of air with constant inflow of oxygen. In the method utilizing MRE degrading liquid in the environment without aqueous solution with inflow of oxygen (referred to as MRE dry degrading method), the influence of molecular chaperon need to be considered for conduct of an enzyme at high temperature area. This is because the inventors discovered surprising fact that the mother cell lytic enzymes and spores of bacterium group such as an MRE symbiotic bacterium group, which is not thermophile, maintain high degrading power at high temperature area of 60-70° C. However, the mother cell (nursing cell) itself cannot survive for a long period of time at this temperature.

Supporting proteins including type II molecular chaperon which offer heat resistance to an enzyme or pre-folding which support the molecular chaperon, and sHSP (short heat-shock protein) are known to have a property to protect enzyme groups having various degrading power at high temperature area. Spores easily germinate by heat shock in the high temperature area. Because a gene of sigma factor which serves as a trigger of sporulation and a trigger gene of HPS released by heat shock are the sigma genes of same class, mother cell lytic enzymes of sporulation are protected by HPS, the molecular chaperon. A molecular chaperon such as HPS works not to push a lipophilic group outside an enzyme and protects an enzyme from denaturing and concentrating. The internal temperature of an enzyme is low to maintain the capability of enzyme reaction because reactive site of an enzyme is inside, hydrophilic group side. In the state of high temperature, energy supply from ATP offered by bacterium or thermal motion places the protected degrading enzyme back to its activated state, and if the material to be degrade is porousness, it is possible to retain degrading power, like thermophile, by exhibiting degrading power of porous hollow in an enzyme at low temperature.

If the material to be degraded is rich in an organic material which serves as nutrition, digestive enzyme group and mother cell lytic enzymes of a germinated nursing cell exhibit synergetic effect and rapidly degrade the organic material. In this process, bone and the like which was traditionally categorized as residue are easily decomposed. On the other hand, if a material to be degraded is oligotrophic or persistent fibrous material, bacterial body, which was germinated and became a nursing cell, is again sporulated and release/supply mother cell lytic enzymes, and the degrading power will be further enhanced. Repeating this re-sporulation process a number of times create more powerful degrading power. Although it is phenomenon in solution, in a comparison experiment of degrading power between culture medium and post-sporulation solution, the reason for backward shift of peak of degrading power on temporal axis for "*Agaricus Blazei* Murill" and "scale of sea bream" may be because infinitesimal quantity of residual spore exist, which strengthened a complementary cell lyase and enhanced the degrading power through re-sporulation process.

Now, a culture method of symbiotic bacterial body including aerobic gram-positive bacterium and/or gram-negative bacterium used in this invention, and a specific method to obtain post-sporulation mother cell lytic enzymes are described. First, culture medium of single or mixed bacterial group including aerobic gram-positive bacterium or gram-negative bacterium is subject to fluid culture under the following culture condition: culture pH 6.0-6.8, culture temperature 25-30° C., and dissolved oxygen level 0.1 mg/L-1.0 mg/L adjusted by aeration. Mineral including fish flour, rice bran, oil meal, meat juice, and magnesium sulfate or silica is given as nutrition of bacterium. In the case of mixed bacterial group, stable symbiotic relation between reciprocal bacterium is waited to be built.

After stabilization of bacterial culture, bacterial group under the state of the nursing cell is separated into another aeration culture tank to continue culture. While aeration is continued in the separated aeration culture tank, all nutrition except silica is then stopped and the culture is placed under starvation state. Around when there are no residual nutrition, sporulation occur utilizing depletion of nitrogen component as a trigger and the solution becomes clear. After confirming completion of sporulation, aeration (oxygen supply) is stopped and the culture is set aside for a while, and the spore (endospore) begin to precipitate concurrently resulting in clear supernatant liquid. The resulting supernatant liquid is filtered through membrane to obtain MRE decomposition liquid. To use it for test of degrading power, the liquid is further filtered through 0.02-μm filter. More specific illustration is shown in Example 1.

The resulting MRE decomposition liquid is used for decomposition of an organic material in the following two methods. To be more precise, one is a method using decomposition apparatus of an organic material with aeration tank; and the other is a method using dry decomposition apparatus of an organic material.

A) The resulting MRE decomposition liquid is separated in an exclusive aeration-culture tank, injected an organic material to be degraded, and added aeration to degrade the organic material. The aeration in this case has a role to agitate and supply oxygen to oxidation-reduction enzyme (refer to Example 2). All apparatus that is needed here is aeration tank to culture aerobic microorganism heretofore known. The decomposition aeration tank for an organic material using MTR decomposition liquid is referred herein to as a "MRE aeration tank."

B) To a decomposition container, an organic material to be degraded is added and agitated while heating to 60-85° C., preferably 64-68° C. Moreover, the resulting MRE decomposition liquid is sprayed to the organic material, continue agitation and heating to decompose the organic material. To the MRE decomposition liquid, small amount of spore obtained in the process manufacturing the MRE decomposition liquid may be added. The decomposition is stopped in smooth super-dry state with moisture content of 5-3%. These apparatus using the MRE decomposition liquid is herein referred to as "heat-mixing dry-type decomposition apparatus," which illustrative embodiment is shown in Example 3.

Regarding to the above B), every time when spores (endospores) is mixed into mother cell lytic enzymes and germination and sporulation is repeated under high temperature and oligotrophic environment, new mother cell lytic enzymes may be supplied and the degrading power may be increased. (This is because the temperature and nutrition state of the whole degrading product becomes unequal and re-sporulation is repeated but not done only one time.) At the last stage, super-aridification occurs by its own effect and sporulation becomes impossible with no bacterium. If this last product is immersed into water, bacterial group used in decomposition extinguishes and anaerobic bacteria which existed inside the organic material to be decomposed, for example, coagulans, are found to barely survive.

Here, an apparatus which may perform the method related to this invention is described. The method related to this invention may be performed using the above heat-mixing dry-type decomposition apparatus; however, the apparatus which may perform the method related to this invention is not limited to the heat-mixing dry-type decomposition apparatus. In addition, one example of the heat-mixing dry-type decomposition apparatus is as following. First, to 60-L decomposition tank, a horizontal axis of rotation is installed, to which four arms fixed to a pair of two stirring plates are installed; and the gradient of the stirring plate is adjusted so that an organic material to be degraded may be evenly agitated. Furthermore, a heating plate is formed along a trajectory of the stirring plate fixed to the rotation axis; and a heater is installed, which is able to regulate temperature of the heating plate between 60-160° C. To the heating plate, one or more temperature sensor is set to measure internal temperature of an organic material to be degraded, without contacting to an agitation plate.

The axis of rotation is adjusted to 2-5 rotations (preferably 4 rotations) per minute through a decelerating apparatus connected to a motor. In addition, adequate space is reserved at the top of the decomposition tank and a slot is set up on the top to inject the organic material to be decomposed. In the superior space, a spray nozzle is installed to evenly spray the MRE decomposition liquid. Furthermore, injection nozzle and exhaust duct is set up to spray air from the top of the decomposition tank downward along the wall by air pump and the exhaust duct is connected to a deodorization equipment as appropriate.

The heating plate of the heat-mixing dry-type decomposition apparatus constituted as above is heated to proper temperature (64-68° C.) and an organic material to be degraded is injected, rotating the agitation plate at the rate of 3-4 rotation per minute. In addition, at the time when the organic material to be degraded is at the proper temperature, proper amount (around 1 liter, in this case) of MRE stock solution for decomposition which is diluted 50 times is sprayed from the injection nozzle to start decomposition process.

When an organic material to be degraded, which water is highly discharged, is degraded in this apparatus, fluid bed is injected. In the present invention, materials which can be used as the fluid bed include, but not limited to, materials with high lignin content such as "rice hull," "bamboo decomposing product," and "sawdust" with slow decomposition rate in this apparatus.

All decomposition products degraded in this heat-mixing dry-type decomposition apparatus have noteworthy characteristics. Unlike the decomposition of an organic material by digestive enzyme of a bacterium, etc., in the heat-mixing dry-type decomposition apparatus of this invention, which is an decomposition apparatus of an organic material mainly using lysosome homologous enzyme, the decomposition product has the following two characteristics.

First, the characteristics include "being super-dry state," and further, it is noteworthy that the characteristic continue more than one year. Unlike a decomposition product formed by the other principle, the decomposition product formed by the heat-mixing dry-type decomposition apparatus reaches to the super-dry state with usual moisture content of 3-5%. In a decomposition product with high moisture content, the moisture content did not exceed 8%. In addition, it became clear that, although this decomposition product gets wet when moisten with water, it has astonishing nature that it maintain super-dry state more than one year after it is left in an usual open depot.

Second, it is characterized as "not going off." This characteristic may come from the first one, and the decomposition product of the heat-mixing dry-type decomposition apparatus is characterized as not getting moldy at all and not going through putrescence by other bacterium or fermentation by lactic acid bacterium; even if odor of the decomposition product is left, it tends not attract flies and differs from decomposition product formed by other principle.

Here, if we refer to usable bacterium in this invention, there are three kind of endospore (spore)-forming bacterium: aerobic gram-positive bacterium, aerobic gram-negative bacterium, and aerobic thermophilic bacterium. Preferably, a non-pathogenic bacterium is used.

The aerobic gram-positive bacterium is a group of bacteria including *Baccilus* sp., *Sporelactobacillus* sp., *Paenibacillus* sp., *Aneurinibacillus* sp., and high-level salt-tolerant alkalophilic *Oceanobacillus* sp., specifically *Bacillus alcel*, *Bacillus cirulans*, *Bacillus licheniformis*, *Bacillus megaterium*, *Bacillus pumilus*, *Bacillus subtillis*, *Bacillus thuringiensis*, *Bacillus lentimorbus*, *Bacillus alvei*, *Bacillus macerans*, *Bacillus polymyxa*, *Bacillus popilliae*, *Bacillus coagulans*, *Bacillus stearothermophilus*, *Bacillus thermoruber*, *Bacillus acidocaldarius*, *Bacillus acidoterestris*, *Bacillus ayclohepttainicus*, *Bacillus alginalyticus*, *Bacillus azotoforians*, *Bacillus badius*, *Bacillus pasteurii*, *Bacillus aminovrans*, *Bacillus marinus*, *Bacillus pusteurii*, *Bacillus sphaericus*, *Bacillus benzoevorans*, *Bacillus fastidiosus*, and *Bacillus nagunoensis*.

The aerobic gram-negative bacterium is a group of bacteria which characterized as apathogenic spore-forming aerobic gram-negative bacterium such as *Comamonas* sp. Specifically, it includes *Comamonas denitrificans* (MK-003) used in Example 1.

The aerobic thermophilic bacterium is a group of bacteria including *Brevibacillus* sp., *Thermobacillussp.*, *Geobacillussp.*, acidophilic high-temperature *Alicyclobacillus* sp. or *Sulfobacillus* sp. *Ureibacillus* sp. *Anoxybacillus* sp. specifically, *Brevibacillus brevis*, *Bacillus stearothermophilus*, *Bacillus coagulans*, *Bacillus flavothermus*, *Bacillus kaustophilus*, *Bacillus pallidus*, *Bacillus schlegelii*, *Bacillus smithii*, *Bacillus thermocatenulatus*, *thermocloacae*, *Bacillus thermodenitrificans*, *Bacillus thermoglucosidasius*, *Bacillus thermoleovo-rans*, *Bacillus thermoruber*, and *Bacillus tusciae*.

In an embodiment of this invention, particularly MRE symbiotic bacteria, which is symbiotic bacterium group of aerobic gram-positive bacteria and gram-negative bacteria, are used. These bacteria are the MRE symbiotic bacterial group described in PCT/JP2010/001120; in other words, the five bacterium groups, comprising this MRE symbiotic bacterial group, consist of aerobic gram-positive *Bacillus* sp. (assignment no. FERM BP-11209, identification no. MK-005), *Lysinibacillus fusiformis* (assignment no. FERM BP-11206, identification no. MK-001), *Bacillus sonorensis* (identification no. MK-004), *Lysinibacillus* sp. (assignment no. FERM BP-11207, identification no. MK-002), and aerobic gram-negative *Comamonas* sp. (assignment no. FERM BP-11208, identification no. MK-003).

This MRE symbiotic bacterial group itself characterizes stable symbiotic body. For example, it was found that usual culture of bacillus create stable population only after filament formation has started under the condition of high density and high nutrition, while low bacterial density of less than 7,000/mL resulting in unstable culture may provide stable culture. This stability was confirmed to continue even at high density.

The degrading power of the mother cell lytic enzymes obtained from the MRE symbiotic bacterial group was found not only to exceed that of bacterial body, including usual bacillus, regarding to protein degrading ability, fatty-acid degrading ability, and polysaccharide degrading ability, but to have ability to degrade higher protein structure including collagen tissue, oils and fats which is not degraded by an existent bacterium, and higher polysaccharide structure and glycoprotein of mushroom which is usually persistent.

In addition, it was confirmed that they have versatile and active degrading effect in high temperature area of 60-75° C. The inventors also discovered that they have an ability to degrade a material which cannot be degraded by traditional thermophilic bacterium, such as *Brevibacillus brevis*, including, for example, "soybean curd refuse," potato refuse, bamboo, and wood. This ability is derived from a property of a lysosome homologous enzyme which is characterized by activating at higher temperature area than a digestive enzyme.

Here, if we describe about a property of an enzyme (MRE) in this invention, an example of an organic material confirmed to be degraded by the MRE includes protein digested by general digestive enzyme, carbohydrate such as starch and glycogen, and edible fat and oil in addition to the following.

Formation of low-molecular compound from polymeric peptide including denatured enzyme and structure protein, decomposition of all kind of amino acid, and low-molecular compound formation and decomposition of collagen I-V, and decomposition of glycoprotein. In addition, decomposition of fat and fatty acid including triglyceride, diglyceride, monoglyceride, saturated fatty acid, unsaturated fatty acid, medium-chain fatty acid, short-chain fatty acid, and cholesteryl ester. Furthermore, decomposition of mucopolysaccharide including dermatan sulfate, heparan sulfate, keratan sulfate, and chondroitin sulfate. Decomposition of sphingolipid including sphingolipid, sphingomyelin, ganglioside, and ceramide. Decomposition of sugar chain and glycoprotein which components include fucose, mannose, sialic acid, N-acetylglucosamine, and glucose. These natures come down to lysosome enzyme group.

Examples of an organic material confirmed to be degraded by MRE, which are generally said to be difficult to be degraded and are difficult or require markedly long time to be degraded by an enzyme secreted from a nursing cell of traditional yeast, *bacillus* sp., and *Aspergillus oryzae*, and various thermophilic bacterium, are as following.

Proteolytic ability is for (1) higher protein structure such as fibrous collagen, (2) higher protein structure of type IV collagen such as basal membrane, (3) ability to disconnect and tear apart a bond of cellular tissue in a plant and an animal, and (4) a tissue binding with calcium phosphate such as collagen and apatite in bone, scale, shell, eggshell, teeth of an animal.

Degrading ability of polysaccharide also includes (1) decomposition of kichin-chitosan of crustacean, (2) decomposition of fiber structure including cellulose and lignin in soybean curd refuse, potato refuse, bamboo, wood, etc., and (3) decomposition of higher polysaccharide structure or glycoprotein of mashroom As for degrading ability of lipid, various types of fatty acid not degraded by an existing bacterium are degraded. In addition, degrading ability of a low-molecular substance includes (1) elimination of bad odor component including ammonia, hydrogen sulfide, and amines, (2) decomposition of catechin in tea leaves, (3) decomposition of capsaicin, and (4) decomposition of pigment in stained sludge. However, the organic material of this invention does not include paraffinum liquidum including petroleum liquid, and a product produced from paraffinum liquidum Meantime, the organic materials described above are only one example of an organic material to be degraded by the method related to the present invention and it goes without saying that the organic material to be degraded by the method related to the present invention is not limited to these.

The technical effects of this invention is the following three points as already described above: (a) the degrading speed is faster than the fermentation by a usual nursing cell, the molecular weight of the decomposition product is lower, and persistent material in usual condition can be easily degraded, (b) low-molecular decomposition product is left unabsorbed by a nursing cell, and (c) it has excellent degrading ability and super-dryness when used in high temperature area (60-70° C.) with air inflow.

A new degrading method of an organic material in this invention applying the above effects provides two industrially useful effects. One is formation of a useful material and the other is decomposition of waste.

First, examples of the useful material include:

A1: decomposition product of "mushroom;" A2: decomposition product of "scale of a fish," A3: decomposition product of "soybean curd refuse," and A4: decomposition product of "bamboo, lumber obtained from thinning, and rice straw."

The decomposition products of waste include:

B1: decomposition of "animal excrement" such as pigs, birds, human, and cows; B2: decomposition of "pesticide residue" including herbicide; B3: decomposition of "waste fat;" B4: decomposition of "garbage;" and B5: decomposition of "stained sludge." Acanthaster devastating coral and jellyfish infesting dirty tea can be also degraded.

These decomposition methods used include "MRE aeration tank" or "heat-mixing dry-type decomposition apparatus." Another grease trap equipment is used for decomposition of "waste fat."

Decomposition products of "mushroom," including for example, *Agaricus* Blazei Murill, *Ganoderma lucidum*, *Cordyceps Sinensis* Berkeley Saccardo, and Chaga are degraded in the aeration tank for MRE decomposition liquid to obtain low-molecular decomposition product of sugar chain. This solution of "mushroom" decomposition products have around 20% higher innate immune activity (including secretion of IFN-α and -β, macrophage activity, and NK activity) than MRE stock solution.

The decomposition product of "scale of fish" can be an excellent basic ingredient of natural immunity activating beauty essence containing collagen and oligopeptide. Particularly, collagen in scale of large sea bream can be degraded into tripeptide and oligopeptide area and let it be absorbed directly from skin. It is well known that tripeptide and oligopeptide is absorbed from skin or mucosa five time higher than amino acid. In addition, because low-molecular bacterial substance degraded by mother cell lytic enzymes is included, macrophage and fibroblast cell of deeper portion than a Langerhans cell or keratinocyte of natural immunity cell system and dermis are activated to facilitate englobement of melanin and reassembly of collagen tissue, resulting in normalization of skin trouble such as spot, blotches and freckles, somberness, small wrinkle, and blemish area to contribute rejuvenation of skin. Here, of note, although a low-molecular decomposition product formed by a usual bacterium is absorbed by bacterial matrix and cannot persist, in the degrading method of this invention, useful low-molecular component such as tripeptide and oligopeptide can persist.

It was discovered that a decomposition product of "soybean curd refuse" works as a safe herbicide. The moisture content of "soybean curd refuse" is about 73% with a high water, and it was difficult to offer degradative treatment. When it is degraded by heat-mixing dry-type decomposition apparatus (an apparatus which continue agitation of a material to be degraded using agitation bar with radiator plate for heating attached to a dry container into which air can flow) using MRE decomposition liquid, degraded residue with super-dry state of not more than 5% moisture is made in about 19 hours. When this "degraded residue of soybean curd refuse" rich in mainly fiber is sprinkled over a rice field, etc., weed which inhibit growth of crops eventually does not grow, so we have a herbicide safe for human and biological system. Especially, it has a nature that it selectively inhibits growth of weed which is harmful to growth of rice.

A decomposition material of "bamboo, lumber obtained from thinning, and rice straw" can be an effective raw material for ethanol. If a material including bamboo, lumber obtained from thinning, or rice straw is cut into 1-15 cm pieces and degraded by a heat-mixing dry-type decomposition apparatus (an apparatus which continue agitation of a material to be degraded using agitation bar with radiator plate for heating attached to a dry container into which air can flow) using MRE decomposition liquid, smooth and coarse powder or short needle-shaped decomposition product, which main components are cellulose, hemicellulose, and lignin, are formed in about 48 hours. This decomposition product may be an optimum raw material to make sugar from direct fermentation/oxygen degradation or supercritical fluid technique or ethanol as an alternate energy.

Although disappearance from direct spraying to excrement is effective in a similar way as bacterial body, decomposition of "animal excrement" can be rather treated in short period of time by a heat-mixing dry-type decomposition apparatus using MRE decomposition liquid.

For example, it is known that usual microorganism cannot easily degrade cattle feces rich in indigestible fiber. However, when the cattle feces are degraded by the heat-mixing dry-type decomposition apparatus using MRE of this invention, we can obtain smooth super-dry powder residue in about 16 hours. This residue can be used in agriculture, or as an alternate fuel, or for production of ethanol.

Decomposition of "waste fat" is performed by dropping MRE decomposition liquid into a grease trap.

In decomposition of "garbage," processing speed is faster than a garbage disposer using a bacterium, and the characteristic of the treatment is that nearly super-dry residue can be obtained in moisture content 6.5% within 15-20 hours without residue such as bone, and of course, bad odor inherent in garbage is removed. The residue can be used as alternative compost for gardening or crops.

In decomposition of "sludge" including stained sludge, the sludge obtained by sanitary sewage treatment using a traditional anaerobic microorganism was harmful and has terrible bad odor. In addition, the problem was that there is no post-treatment method for stained sludge. When this "sludge" including stained sludge is degraded by the heat-mixing dry-type decomposition apparatus using MRE decomposition liquid, super-dry (about 4.5%) residue is obtained in 21 hours. This residue has no bad odor with perfume of soil and can be used directly as a fuel or alternate compost for agriculture.

Because an innate immune complex ligand of this invention is a water-soluble low-molecular-weight substance in oligo region without polarity, it has a nature to penetrate easily through skin and can be used as a beauty essence penetrating to dermis. By applying the natural immune complex ligand of this invention over face or body, it can be used as a natural immunity activating beauty essence.

The natural immunity activating complex ligand may activate a Langerhans cell which is a member of macrophage in epidermides and facilitate phagocytosis of melanine flowing out from keratinocyte destroyed by ultraviolet, etc., having advantageous effect to get pigmented spot off, recover sunburn, improve dullness of skin, and offer transparency to skin.

In dermis, it can erase fine lines and improve large lines by activating macrophage and making cross-linkage in combination with fibroblast and remodeling old collagen. In addition, the activation of macrophage can improve blemish. In fact, it is observed that white head and fat mass are diminished.

The nature to inhibit inflammation of the complex ligand of this invention was confirmed to have inflammatory suppression effect in inflammation of sunburn or acne and atopic dermatitis.

EXAMPLE

The following examples illustrate an embodiment related to the present invention.

Example 1

Manufacture of MRE Decomposition Liquid for Decomposition of an Organic Material Culture of an MRE symbiotic aerobic bacterium group is performed by general culture method of an aerobic gram-positive bacterium. To a 1.2-$m^3$ culture aeration tank, 1000 L of water is added to aerate. To the culture aeration tank, 3 kg of fish flour, 3 kg of rice bran, 1.3 kg of oil meal, and 350 g of meat juice are added as nutrition, and further, adequate dose of a mineral such as magnesium sulfate and silica is added. Furthermore, bacterial body is injected to culture an MRE symbiotic bacterium group while adding aeration to make dissolved oxygen level 0.5 mg/L to 1.2 mg/L under the culture condition of culture pH 6.0-6.8 and culture temperature 25-35° C.

After adequate multiplication and stabilization of a bacterium, the MRE symbiotic bacterium group is placed under starvation state without any nutrition, and further continue aeration under the condition of 15-35° C., resulting in initiation of endosporulation of the MRE symbiotic bacterium group using depletion of nitrogen component as a trigger. After steep increase of clarity of the culture medium, aeration (oxygen supply) is stopped and the endospore concurrently initiates precipitation to make clear solution. The resulting clear supernatant liquid is then placed under pressure filteation through 0.2-μm membrane to obtain MRE decomposition liquid containing mother cell lytic enzymes. The timing of stopping aeration can be determined after completion of sporulation under phase microscope is confirmed.

Example 2

Decomposition of "True Sardine" in Mer Aeration Tank 450 mL of MRE decomposition liquid obtained in Example 1 was diluted with water, and 458 g of 12 true sardines was degraded under the condition of temperature 22-28° C. and pH 6.0-7.0. The aeration was performed while agitating for the purpose of agitation and resupply of oxygen necessary to oxidation-reduction enzyme. The required oxygen was a little, so it was not checked by DO meter. Culture medium and MRE decomposition liquid were compared under the same condition.

Four days later, the "true sardine" was completely degraded including bone. When the same "true sardine" is degraded by the heat-mixing dry-type decomposition apparatus, it reached to super-dry state within only 3 hours.

The bone in the culture medium was not completely degraded and 36 g of precipitation residue was obtained. The MRE decomposition liquid became completely clear and the precipitation residue was 6.2 g with ash of more than 99%. Analytical result of the decomposition liquid was the following: water content, 99.8 g/100 g (reduced-pressure drying by heating); protein, less than 0.1 g/100 g (Kjeldahl method); lipid, less than 0.1 g/100 g (soxhlet extraction); ash, 0.1 g/100 g (direct incineration); carbohydrate, 0.1 g/100 g (by calculation); energy 0 kcal/100 g (by calculation); sodium 28.3 g/100 g (atomic absorbance determination); and no eicosapentaenoic acid and docosahexaenoic acid detected by gas chromatography.

Example 3

Decomposition of "Cattle Feces" by the Heat-Mixing Dry-type Decomposition Apparatus Because feces have high fiber content with low nutrition, the decomposition in a decomposition method using traditional microorganism was difficult. The cattle feces were degraded by the following heat-mixing dry-type decomposition apparatus.

The heat-mixing dry-type decomposition apparatus has a 60-L decomposition tank installing a horizontal axis of rotation, to which two pairs of four stirring plates are fixed; and adjust the gradient of the stirring plates so that a material may be evenly agitated Moreover, a heating plate is formed along a trajectory of the stirring plate fixed to the rotation axis; a heater which is able to regulate temperature of the heating plate between 60-160° C. is installed; and the heater is adjusted so that an material to be heated reaches to 60-80° C., preferably 64-68° C. The axis of rotation is adjusted to 2-5 rotations (preferably 4 rotations) per minute through a decelerating apparatus connected to a motor. At the top of decomposition tank, a spray nozzle is installed to blow air through air pump from top of the decomposition tank downward. In addition, a spray nozzle is installed to evenly spray the MRE decomposition liquid to the top of decomposition tank.

The heating plate of the heat-mixing dry-type decomposition apparatus configured like this is heated to proper temperature, turned around 3-4 rotation per minute with agitation plate, and an organic material to be degraded Moreover, decomposition process is initiated by spraying the MRE decomposition liquid first from proper-dose spraying nozzle.

To this heat-mixing dry-type decomposition apparatus, 50 kg of "cattle feces" was injected; 7 kg of "rice hull" with slow decomposition rate was added as a fluid bed; the mixture was adjusted and agitated to maintain surface temperature of "cattle feces" to be degraded 70° C.; and the MRE decomposition liquid obtained in Example 1 was diluted 50 times and sprayed. After 16 hours, the "cattle feces" diminished to 5 kg and reached to super-dry state of moisture content 3.2%. The "rice hull" also became smooth powder not retaining the original form.

Residue of the "cattle feces" was all fiber similar to the decomposition product of "rice hull" when observed by microscope. The "rice hull" was confirmed to further enable continuation of decomposition. It was found that pig or chicken feces can be easily degraded and used as compost.

Example 4-1

Decomposition of "Scale of Sea Bream (Scale Collagen)" in MRE Aeration Tank and Usefulness of the Decomposition Product Obtained 450 mL of MRE decomposition liquid obtained in Example 1 was diluted with 10 L of water, and 420 g of scale of a large sardine from Taiwan was directly degraded under the condition of temperature 22-28° C. and pH 6.0-7.0 without trituration. Agitation was performed through aeration to meet oxygen demand of oxidation-reduction enzyme. Original form of scale of sea bream was injected to enzyme solution diluted with water without any pretreatment such as trituration or acid treatment. About 60 days later, 92 g of undegraded residue was left in the culture medium, but the scale was almost completely degraded in the MRE decomposition liquid with 0.6 g of ash residue left.

The molecular weight of the degraded peptide from collagen in the decomposition liquid was measured by exclusion chromatography using TSKgel/G2500PW column for distribution of molecular weight. The chromatogram for measured result of this distribution of molecular weight is shown in FIG. 1, and when the distribution of molecular weight is compared to that of standard preparation for molecular weight, more than 10,000 was trace, 3000-10,000 was 1%, 1000-3000 was trace, 500-1000 was trace, and less than 500 was 99%. In decomposition of culture medium, useful low-molecular decomposition product did not remain because it was digested and absorbed by a mother cell of a bacterium.

In addition, as a result analyzing free amino acid of scale decomposition liquid of this example, content of amino acid was less than detection limit. This fact strongly suggests that oligopeptide constitutes low-molecular component of the scale decomposition liquid. Oligopeptide is known to be absorbed easily from skin and mucosa, because it does not have extreme charge and polarity like amino acid, and to contaminate into blood after reaching to dermic layer of skin even if the sequence is 12 amino acids.

In addition, ⅓ of scale collagen peptide includes glycine and significant amount includes proline and hydroxyproline specific to collagen. Because these components can reach to dermis in the form of oligopeptide, it goes without saying that it may be an important nutrient material for remodeling of old collagen such as wrinkle. When the resulting scale decomposition liquid is filtered through 0.02-μm filter to use it as a beauty essence, it was then excellent as natural immunity activating beauty essence.

Example 4-2

Application of Scale Collagen Decomposition Product to Beauty Essence

The MRE decomposition liquid of this example contains the "natural immunity ligand" of Application filing no. 2009-

61956. This "natural immunity ligand" activates Langerhans cell and keratinocyte derived from natural immunity cell which exist in epidermis of skin. The Langerhans cell is a fellow natural immunity cell of macrophage derived from bone marrow and is known to phagocytize and degrade melanine leaked outside cell upon destruction of keratinocyte. Therefore, it can improve flecks and age spot which is not cosmetically preferable. Activation of keratinocyte activates metabolism of skin and rejuvenates skin cells. In addition, because the keratinocyte is closely related to growth of hair, it is observed that heavy lanugo hair starts coming through when the scale decomposition product is applied to an egg-like bald head.

The natural immunity ligand component penetrating to dermis activates a macrophage existing in the dermis or dermal capillaries. Activated macrophage then cooperates with fibroblast, and old collagen fiber is remodeled using scale collagen of the decomposition component as a nutritional substance. These old and rigid collagen of dermic layer is remade which leads to rejuvenation of the dermic layer, and wrinkles (especially file lines) and blemish areas are remarkably improved. The characteristic of this improvement is not to be accompanied by misery from inflammation of laser beam or tretinoin therapy.

Examples of a beauty essence of scale decomposition component using MRE decomposition liquid as described above include:

(1) 75-year-old female, who was troubled by sunburn, skin disorders, and fine wrinkles due to vegetable gardening. She used 1-3 mL/day. She was surprised by temporally whitened skin at the moment when she applied the beauty essence for the first time, and about one month later, her face turned into white with less fine wrinkles. Currently, 6 months later, she appreciates shiny, beautiful, normal flesh color.

(2) 58-year-old female, who used steroid for a long period of time for atopic dermatitis in childhood, and at that time, freckled all over her face triggered by climbing. She used 2-3 mL of the beauty essence every morning. Several months later, her complexion just turned into good condition and her freckles got thin. One year later, her freckles became almost unnoticeable and can be covered easily by makeup.

(3) 72-year-old female, who had fine freckle- or fleck-like spot all over her cheeks on both side. She applied 3-5 mL every morning. Her face became clear in one week, and fine freckle-like spot nearly disappeared in a half year. A little bit of spot was left, but was able to be covered by makeup.

(4) 45-year-old female. She used 3 mL of the beauty essence every morning. Her chloasma-like flecks on both cheeks, which lasted a long period of time, became paled out in a half year (5) 50-year-old female. She used approximately 3 mL every morning. About 3 months later, fine wrinkles totally disappeared and her skin became smooth, white, and shiny without thin spot.

(6) 60-year-old female. She used 2-3 mL every morning. Her fine wrinkles at the corners of her eyes disappeared in about 3 months, and many white small fat masses existed between forehead, eyes, and temples disappeared in one year without noticing it.

(7) 21-year-old male who had terrible "erupted acne" on his forehead and cheeks and applied 3-5 mL/day in the morning. Inflammation fairly reduced from the next day to day 4, and suppuration was inhibited in one week. His acnes became less prominent in one month.

(8) 23 year-old female who had spots turned from redness of blemish areas and was subject to depression every time she look into a mirror. She used 2-3 mL of this beauty essence every morning. She realized improvement on day 2, and her sustained blemish area became thin in the second week with no need to use a concealer. Her pores also became small.

(9) 82 of 100 persons who used this beauty essence reported improvement of skin luster, fine texture, and increase of transparency of skin, and makeup became easier to apply.

Example 5

Decomposition of Polysaccharide (High Molecular Sugar Chain) of Fungi Such as *Agaricus Blazei* Murill and *Ganoderma Lucidum* Using MRE Aeration Tank and Usability of the Decomposition Product

*Agaricus Blazei* Murill 60% and *Ganoderma lucidum* 40% are decocted for 60 minutes to obtain extract. To 200 mL of MRE decomposition liquid of Example 1, 4.8 L of decocted extract was added to degrade while aerating under the condition of decomposition temperature 25-32° C. and pH 5.8-6.8. The liquid turned into clear completely in about 10 days, and after stopping aeration, precipitation occurred quickly to make 12 g of precipitation residue. As a result of analyzing supernatant solution, the polysaccharide (high molecular sugar chain) was degraded into low-molecular sugar chain with 600-2000 molecular weight (equivalent to 2-12 monosaccharides). No acid including citric acid was used.

When the liquid obtained as above was filtered with 0.02-μm filter and used as natural immunity ligand beverage, about 20% higher natural immune activity was obtained compared to traditional natural immunity ligand beverage (refer to Application filing no. 2009-61956). This was because macrophage activity resulted in 23% higher.

Example 6

Decomposition of Soybean Curd Refuse Using the Heat-mixing Dry-type Decomposition Apparatus and Usability of the Decomposition Product The soybean curd refuse, which was difficult to degrade by traditional microorganism including bacillus and thermophilic bacterium until recently due to its high moisture, high fiber, and oligotrophic nature, was degraded using the heat-mixing dry-type decomposition apparatus.

28 kg of the "soybean curd refuse" was injected into the heat-mixing dry-type decomposition apparatus, agitating and adjusting to maintain surface temperature of a material to be degraded to 65-70° C., and 580 mL of the MRE decomposition liquid obtained in Example 1 and diluted with 3.5 L of water was sprayed to the material to be degraded. Because it contained high fiber component, fluid bed including "rice hull" was not used. The "soybean curd refuse" with 74% moisture content turned into that with 3.2% moisture content of super-dray state in about 28 hours, which reside was 6 kg. All the resides were fibrous when observed with microscope.

In addition, when this "decomposition residue of soybean curd refuse" is spread at the same time as rice planting, weed that inhibits growth of rice does not grow in. It was found to eliminate the need to spray herbicide and can be used for other than rice as a harmless herbicide replacing harmful one.

Example 7

Decomposition of "Bamboo, Lumber Obtained from Thinning, and Rice Straw" and Usability of the Decomposition Product The bamboo, lumber obtained from thinning, and rice straw in question for disposal are degraded using the heat-mixing dry-type decomposition apparatus and can create excellent raw material for production of ethanol. The decomposition product of these materials including bamboo can also be used as compost after fermentation.

Bamboo, rice straw, and weed are cut into 1-cm pieces, lumber obtained from thinning is cut into 10-cm pieces, and 52 kg of the mixture of bamboo, lumber obtained from thinning, and rice straw was injected into the heat-mixing dry-type decomposition apparatus at the weight ratio of 1:1:1. After activating the apparatus, the MRE decomposition liquid diluted 6 times was sprayed. About 48 hours later, 3.3 kg (6.3%) of super-dry powder residue of moisture content 3.8% was obtained.

The analysis of this residue showed that it contains 43.1% of cellulose, 12.6% of hemicellulose, and 25.2% of lignin. The cellulose/hemicellulose and lignin can be directly or indirectly transformed into ethanol fuel using fermentation by microorganisms, decomposition by enzymes, or supercritical fluid. As described above, the residual decomposition product of this example may be an excellent raw material for sugar and ethanol manufacturing. Or this residue can be directly used as a fuel after solidification into a chip, or can be used as a construction material after solidification of residue.

Example 8

An Example of Directly Using MRE Decomposition Liquid (1) MRE decomposition liquid was degraded after it was diluted 20 times with water, sprayed over poultry feces, and covered with a sheet. Bad odor of poultry feces was immediately disappeared and the weight of feces was reduced to 35%. In addition, total decomposition required 20 days. Porcine feces were same as above.

(2) Decomposition in normal temperature range: To 5 kg of cattle feces piled up in the field, 5 L of MRE decomposition liquid diluted 5 times with water was sprayed directly. Immediately after spraying, bad odor disappeared and the volume of cattle feces was decreased by about 20%. The feces were nearly degraded in one month.

(3) To a 5-m$^3$ preserve of Koi, 5 L of MRE decomposition liquid was sprayed. Dirt attached to the wall of the preserve was removed, residue of feed and feces were degraded, and clogging of a filter was resolved. Koi in the preserve had more energy and an increased appetite.

Example 9

Decomposition of Edible Fat and Oil and Fatty Acid 60-cm grease trap attached to an aeration equipment at the depth of 1 m×1 m is aerated. Depending on the nature and volume of fat and oil to be degraded, 30-50 mL of MRE decomposition liquid per day can be dropped to degrade edible fat and oil and fatty acid continuously.

Example 10

Decomposition of Garbage Using the Heat-mixing Dry-type Decomposition Apparatus

When MRE decomposition liquid diluted 10 times is sprayed to "garbage" put into the heat-mixing dry-type decomposition apparatus, bad odor disappeared and the garbage is degraded and turns into smooth super-dry powder residue in 3-20 hours depending on the content. The residue is not corrupted after leaving it aside for one year, and further, shells, bones of a fish and an animal, shell of a crab, feather of a bird, skin of bamboo shoot are also degraded. Furthermore, jellyfish and Acanthaster are easily degraded, both of which present problems in treating in terms of environment concern.

Example 11

Decomposition of "Sludge" Including Stained Sludge

The "sludge," which is residue of microbial treatment of sanitary sewage, was degraded using the heat-mixing dry-type decomposition apparatus. In particular, the sludge treated with anaerobic microorganism has bad odor and presents problems in post-treatment, and the stained sludge has high moisture content which makes post-treatment difficult by a traditional technology.

To the heat-mixing dry-type decomposition apparatus, 40 kg of "stained sludge" was injected and 4 kg of "rice hull" was additionally injected. The sludge was continued to be agitated to retain surface temperature of the material to be degraded 65-70° C. and 220 mL of MRE decomposition liquid obtained in Example 1 was sprayed to this material.

The "stained sludge" turned into dry state with moisture content of 4.3% in about 21 hours and the residue except the weight of rice hull was 7.12 kg (decomposition rate, 82.2%). It was observed that residual particle was considerably fine when observed the residue of the stained sludge with microscope. Bad odor of the stained sludge disappeared and the pigment was also considerably degraded.

The present invention may obviously be modified in a variety of forms, and without limitation to the above one embodiment, may be modified in a variety of forms without changing the argument of the invention.

What is claimed is:

1. A method for degrading an organic material comprising:
preparing an organic material to be degraded; and
applying to the organic material an effective amount of a solution that comprises mother cell lytic enzymes formed through cytolysis associated with spore formation in a group of symbiotic, endospore-forming, aerobic bacteria that comprises *Bacillus* sp., *Comamonas* sp., *Lysinibacillus* sp., *Bacillus sonorensis*, and *Lysinibacillus fusiformis*.

2. The method of claim 1, further comprising:
applying to the organic material spores formed from the spore-forming aerobic bacteria, wherein the spores form mother cell lytic enzymes through germination and re-sporulation.

3. The method of claim 1, wherein the organic material is immersed in a solution comprising the mother cell lytic enzymes or the spores, and is decomposed by aerating the solution.

4. The method of claim 1, wherein the organic material is selected from the group consisting of *Ganoderma lucidum*, *Agaricus blazei* (Murill), *Cordyceps sinensis* (Berkeley) (Saccardo), chaga, and fish scale.

5. The method of claim 4, wherein the organic material comprises fish scale.

6. The method of claim 3, wherein the organic material is decomposed by spraying the organic material with a solution that comprises the mother cell lytic enzymes or the spores.

7. The method of claim 6, wherein the organic material comprises a high lignin-containing material selected from the group consisting of rice hulls, rice straw, bamboo, and sawdust.

8. The method of claim 6, performed using an apparatus that comprises:
- a decomposition tank having a horizontal axis of rotation, about which one or more arms with a fixed stirring plate are installed, the tank being adapted to form a heating plate along a trajectory of the stirring plate,
- a heater, which is able to regulate temperature of the heating plate between 60-160° C.; and
- a nozzle installed at the top of the decomposition tank, adapted to spray the solution onto the organic material or to introduce air into the decomposition tank.

9. The method of claim 8, wherein the organic material comprises soybean curd refuse.

10. The method of claim 6, wherein the organic material comprises bamboo, sawdust, rice straw, lignin, or cellulose.

11. The method of claim 3, wherein the solution is aerated by stirring at a temperature of 60 to 80° C.

12. The method of claim 4, wherein a decomposition product of the degraded organic material is a natural immunity-activating composition.

13. The method of claim 6, wherein the organic material comprises a decomposition product of mushrooms, fish scale, soybean curd refuse, potato refuse, bamboo, wood, rice straw, animal excrement, pesticide residue, waste fat, sludge, or refuse.

14. The method of claim 9, wherein a decomposition product of the soybean curd refuse is used as a chemical herbicide.

15. The method of claim 10, wherein a decomposition product of the organic material is used for the production of ethanol.

16. The method of claim 1, wherein a population of symbiotic, spore-froming aerobic bacteria comprises *Lysinibacillus fusiformis* FERM BP-11206, *Lysinibacillus* sp. FERM BP-11207, *Comamonas* sp. FERM BP-11208, *Bacillus* sp. FERM BP-11209, and *Bacillus Sonorensis*.

17. A method for degrading an organic material, comprising:
- (a) preparing an organic material to be degraded; and
- (b) applying to the organic material an effective amount of a composition that comprises a solution of degradative enzymes obtained from sporulation-associated cytolysis of mother cells of a group of symbiotic, endospore-forming, aerobic bacteria that comprises *Lysinibacillus fusiformis*FERM BP-11206, *Lysinibacillus* sp. FERM BP-11207, *Comamonas* sp. FERM BP-11208, *Bacillus* sp. FERM BP-11209, and *Bacillus sonorensis*.

18. The method of claim 17, wherein the organic material comprises a decomposition product of mushrooms, fish scale, soybean curd refuse, potato refuse, bamboo, wood, rice straw, animal excrement, pesticide residue, waste fat, sludge, refuse, or a combination thereof.

* * * * *